United States Patent [19]

DeVenuto

[11] Patent Number: 5,456,687
[45] Date of Patent: Oct. 10, 1995

[54] METHOD AND APPARATUS FOR INSERTING AND INTRACULAR LENS

[76] Inventor: Joseph DeVenuto, 2955 Sugan Rd., Sulbury, Pa. 18963

[21] Appl. No.: 396,076

[22] Filed: Feb. 28, 1995

Related U.S. Application Data

[63] Continuation of Ser. No. 230,426, Apr. 19, 1994, abandoned, which is a continuation of Ser. No. 973,996, Nov. 10, 1992, abandoned.

[51] Int. Cl.⁶ ........................................... A61F 9/00
[52] U.S. Cl. ............................................. 606/107
[58] Field of Search ..................... 606/228, 151, 606/107, 113; 623/4, 6

[56] References Cited

U.S. PATENT DOCUMENTS

| | | | |
|---|---|---|---|
| 4,538,611 | 9/1985 | Kelman | 606/113 |
| 4,747,404 | 5/1988 | Jampel et al. | 606/107 |
| 4,917,680 | 4/1990 | Poley | 623/6 |
| 5,176,686 | 1/1993 | Poley | 623/4 |
| 5,190,553 | 3/1993 | Kanert et al. | 623/6 |

*Primary Examiner*—Tamara L. Graysay
*Attorney, Agent, or Firm*—Steve Mendelsohn; William H. Murray

[57] ABSTRACT

A method and apparatus for inserting a foldable intraocular lens into an eye. The lens is grasped and inserted through an incision in the eye with a forceps, while the lens is held in a folded state within the loop of the apparatus. After positioning the lens within the eye, the tail of the apparatus, which extends outside the eye through the incision, is pulled to slide the loop off the lens, thereby allowing the lens to unfold. The invention is also a method and apparatus for folding the lens and placing the folded lens within the loop of the apparatus for insertion into the eye.

19 Claims, 4 Drawing Sheets

METHOD AND APPARATUS FOR INSERTING AND INTRACULAR LENS

This is a continuation of application(s) Ser. No. 08/230,426 filed on Apr. 19, 1994, now abandoned which is a continuation of Ser. No. 07/973,996 filed on Nov. 10, 1992, now abandoned.

BACKGROUND OF THE INVENTION

1. Field of the Invention

The present invention relates to eye surgery, and, in particular, to a method and apparatus for inserting an intraocular lens into an eye.

2. Statement of Related Art

When a cataract is removed from an eye, the lens may be replaced with an artificial foldable silicone intraocular lens, such as shown in FIG. 1. The lens is inserted into the eye through an incision made in the eye. In general, the smaller the incision, the better for the patient. Conventional devices for inserting the lens into the eye require incisions of at least 4.5 millimeters in length.

SUMMARY OF THE INVENTION

The present invention is a method for inserting a foldable intraocular lens into an eye using a forceps and an apparatus having a loop and a tail. The lens is grasped with the forceps, wherein the lens is held in a folded position within the loop of the apparatus. The lens is inserted into the eye with the forceps through an incision in the eye, wherein the tail of the apparatus extends outside the eye. The tail of the apparatus is pulled to release the lens from the loop of the apparatus.

The present invention is also a method for folding a foldable intraocular lens and inserting the folded lens into a loop using a disk having a groove on a surface of the disk, wherein the groove extends to an edge of the disk. The lens is placed on the disk. The loop is placed next to the end of the groove at the edge of the disk. The lens is folded by forcing the lens into the groove. The folded lens is slid along the groove into the loop.

The present invention is also an apparatus for inserting a foldable intraocular lens into an eye. The apparatus comprises a loop, for maintaining the lens in a folded state, and a tail connected to the loop.

The present invention is also an apparatus for folding a foldable intraocular lens and inserting the folded lens into a loop, comprising a disk having a groove in a surface of the disk and a hollow protrusion, wherein the groove extends to the protrusion.

DETAILED DESCRIPTION OF THE INVENTION

Figure 1:
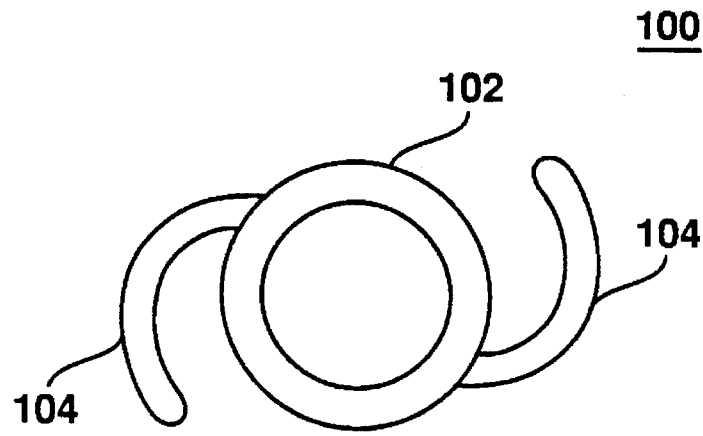
FIG. 1 shows an artificial foldable silicone intraocular lens.

Referring now to FIG. 1, there is shown artificial foldable silicone intraocular lens 100 comprising optic 102 and haptics 104. Lens 100 is typically 6 millimeters in diameter when not in a folded state.

Figure 2:
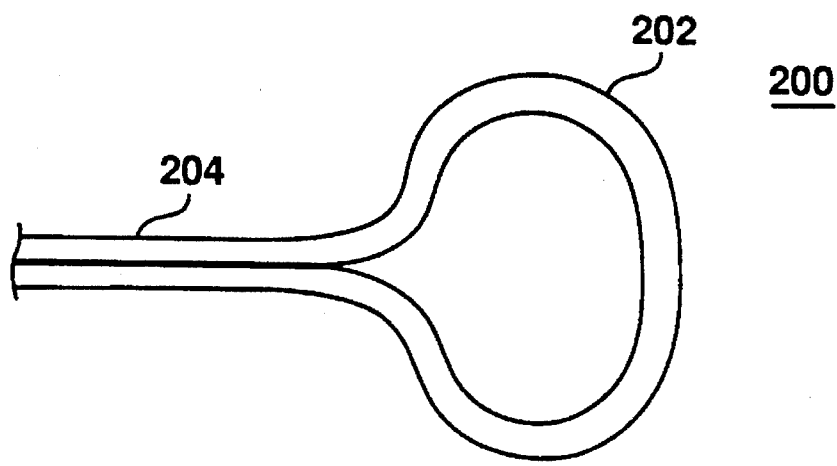
FIG. 2 shows a side view of an apparatus according to the present invention for inserting the lens of FIG. 1 into an eye.

Referring now to FIG. 2 there is shown apparatus 200 according the present invention for inserting lens 100 into an eye. Apparatus 200 comprises loop 202 and tail 204. Apparatus 200 may be formed by partially folding a ribbon of flexible plastic material in half lengthwise. The two ends of the ribbon are held together to form tail 204 either by heating the plastic while pressing the ends together or using an adhesive. Loop 202 is formed by only partially folding the ribbon, that is, by not forming a severe crease in the ribbon. In a preferred embodiment of the present invention, loop 202 has an inner diameter of approximately 2.7 to 2.8 millimeters and tail 204 is at least 40 millimeters long. The ribbon material from which apparatus 200 is constructed is preferably approximately 0.5 millimeters thick and 2.5 millimeters wide. Apparatus 100 may be constructed of a sterilizable plastic such as KEVLAR, manufactured by DuPont.

Figure 3:
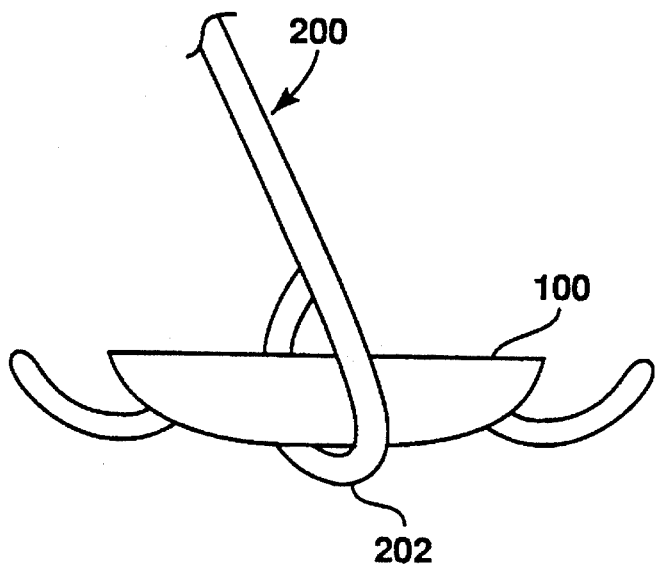
FIG. 3 shows the lens of FIG. 1 held in a folded state in the loop of the apparatus of FIG. 2.
Figure 4:
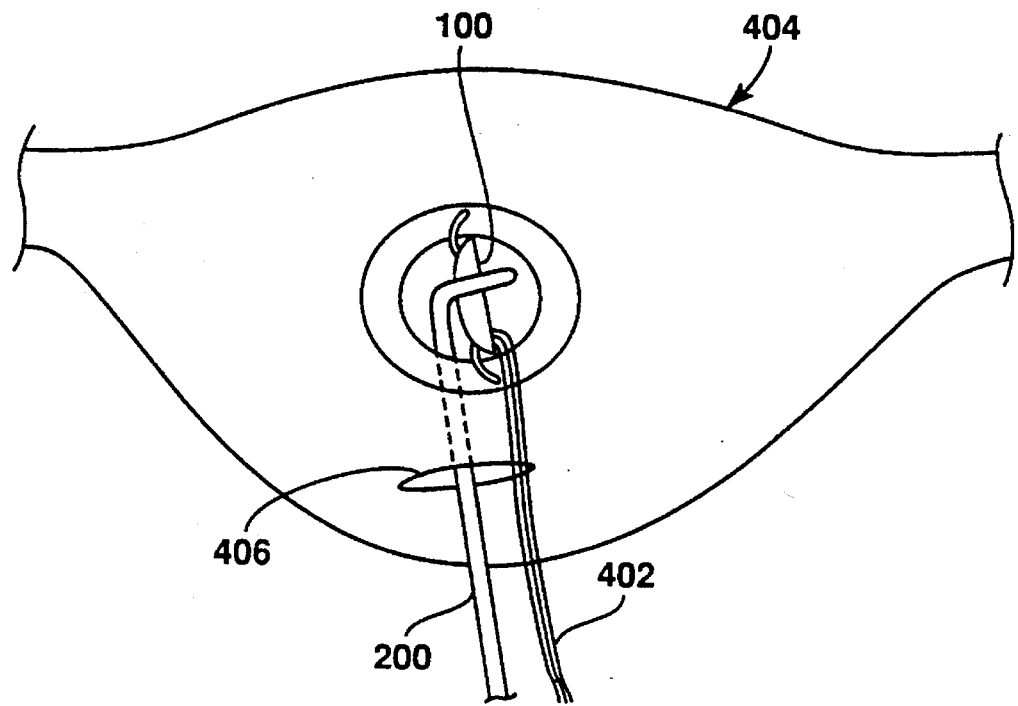
FIG. 4 shows the lens of FIG. 3 being inserted into an eye with a forceps.

Referring now to FIG. 3, there is shown lens 100 held in a folded state in loop 202 of apparatus 200. As shown in FIG. 4, folded lens 100 may be grasped with forceps 402 and inserted into eye 404 through incision 406, while lens 100 is held within loop 202 of apparatus 200. Incision 406 is preferably at most 3.5 millimeters in length. After lens 100 is properly positioned within eye 404, tail 204 of apparatus 200 may be pulled to release lens 100 from loop 202. Lens 100 is then free to unfold within eye 404. As tail 204 is pulled, loop 202 passes over the end of forceps 402. Lens 100 may then be released from forceps 402, which is removed from eye 404 along with apparatus 200 through incision 406.

Figure 5:
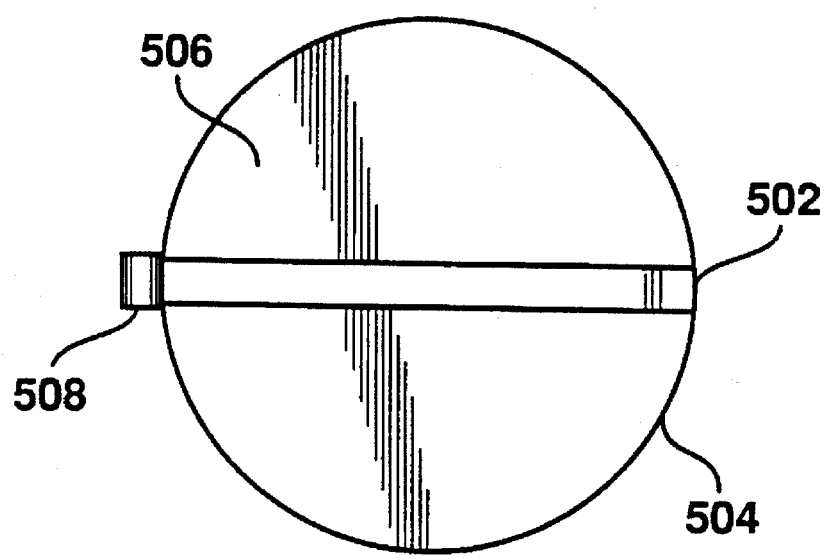
FIG. 5, 6, and 7 show plan, side, and perspective views of the apparatus for folding the lens of FIG. 1 and inserting the folded lens into the loop of the apparatus of FIG. 2.
Figure 6:
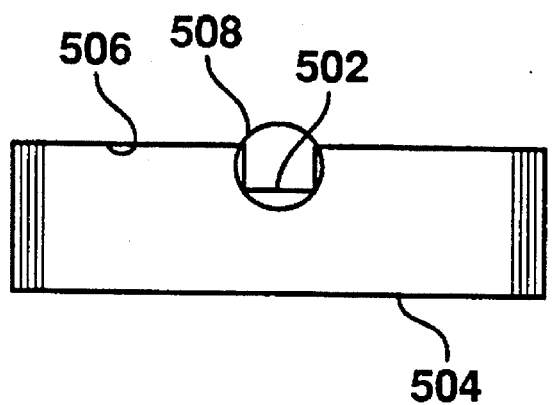
Figure 7:
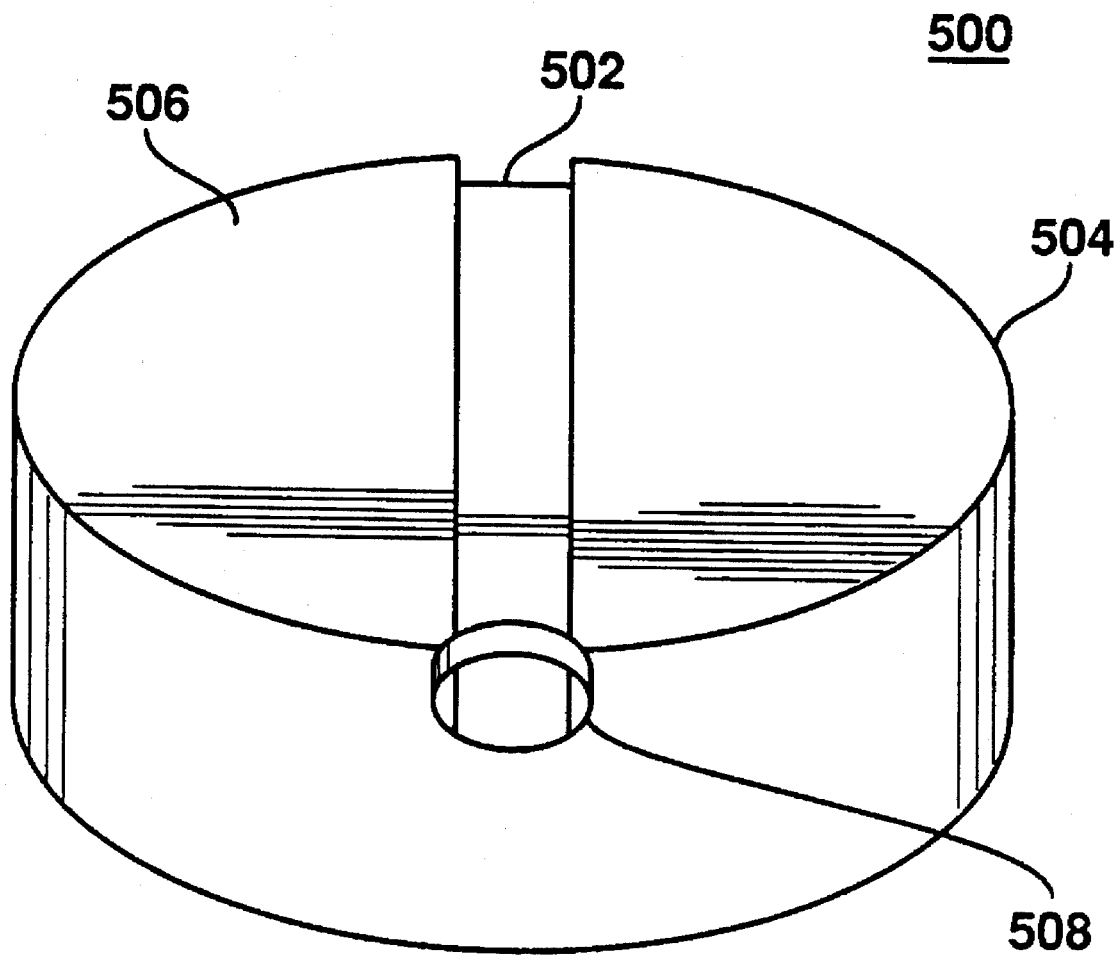

Referring now to FIGS. 5, 6, and 7, there are shown plan, side, and perspective views of apparatus 500 according to the present invention for folding lens 100 and inserting folded lens 100 into loop 202 of apparatus 200. Apparatus 500 comprises disk 504 having groove 502 along surface 506 of disk 504 and hollow protrusion 508 extending from groove 502. Disk 504 may be made of any sterilizable material and is preferably made of a hard smooth plastic that will not damage lens 100. Groove 502 is preferably approximately 2 millimeters wide, 2.8 millimeters deep, and at least 6 or 7 millimeters long. In a preferred embodiment, protrusion 508 has an outer diameter of approximately 2.5 millimeters, which is slightly smaller than the inner diameter of loop 202. Protrusion 508 is preferably about 2.5 millimeters long or roughly equivalent to the width of loop 202. The edges and corners of apparatus 500 are preferably rounded to prevent mechanical damage to lens 100.

According to the present invention, to fold lens 100 and insert it into loop 202 of apparatus 200, loop 202 is placed around protrusion 508 of disk 504 and lens 100 is placed onto surface 506 of disk 504. Using a forceps, lens 100 is forced into groove 502, whereby lens 100 becomes folded. Folded lens 100 is then forced along groove 502 with a forceps toward protrusion 508. Lens 100 is slid out of groove 502 into protrusion 508. With lens 100 extending partially out of protrusion 508, tail 204 of apparatus 200 is pulled to pull loop 202 off protrusion 508 and directly onto lens 100. Loop 202 holds lens 100 in the folded state. Folded lens 100 may then be inserted into eye 404 using the forceps while folded lens 100 is held within loop 202.

According to a preferred embodiment of the present invention, with lens 100 resting over groove 502 near protrusion 508 and loop 202 placed around protrusion 508, lens 100 may be grasped with a forceps from below, with the forceps inserted through protrusion 508. Lens 100 is then folded by pulling lens 100 into groove 502 with the forceps. Lens 100 is then pulled into protrusion 508 with the forceps, where loop 202 is slid off protrusion 508 onto lens 100. Folded lens 100 may then be directly inserted into eye 404. In this preferred embodiment, the entire procedure of folding lens 100, placing loop 202 over lens 100, and inserting lens 100 into eye 404 may be accomplished with one continuous grasp of lens 100 by the forceps, thereby reducing the risk of mechanical damage to lens 100.

It will be understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An apparatus for inserting a foldable intraocular lens into an eye, comprising:
   (a) a tail; and
   (b) a loop, connected to the tail, for maintaining the lens in a folded state and for sliding off the lens while remaining intact as a loop when said tail is pulled to release the lens from said loop.

2. The apparatus of claim 1, wherein said tail is adapted to extend outside the eye through said incision.

3. The apparatus of claim 2, wherein said tail is pulled to release the lens from said loop while holding the lens with the forceps, thereby allowing the lens to unfold, wherein said loop slides over the end of the forceps.

4. An apparatus for inserting a foldable intraocular lens into an eye, comprising:
   (a) loop means for maintaining the lens in a folded state and for retaining the lens in a folded position while the lens is grasped with a forceps and inserted into the eye through an incision in the eye and for sliding off the lens while remaining intact as a loop; and
   (b) tail means, connected to said loop means, for being pulled to cause said loop means to slide off the lens while remaining intact as a loop, to release the lens from said loop means.

5. The apparatus of claim 4, wherein said tail means for extending outside the eye through said incision.

6. The apparatus of claim 5, said tail means for being pulled to release the lens from said loop means while holding the lens with the forceps, thereby allowing the lens to unfold, said loop means for sliding over the end of the forceps.

7. An apparatus for folding a foldable intraocular lens and inserting the folded lens into a loop, comprising a disk having a groove in a surface of said disk and a hollow protrusion, wherein said groove extends to said protrusion and said protrusion is positioned at an edge of said disk.

8. The apparatus of claim 7, wherein said protrusion is adapted to receive said loop.

9. A method for inserting a foldable intraocular lens into an eye using a forceps and an apparatus having a loop and a tail, comprising the steps of:
   (a) placing the lens on a disk having a groove on a surface of said disk and a hollow protrusion, wherein said groove extends to said protrusion;
   (b) placing the loop of the apparatus over said protrusion;
   (c) folding the lens by forcing the lens into said groove;
   (d) sliding the folded lens along said groove into said protrusion;
   (e) slipping the loop off said protrusion and onto the folded lens;
   (f) grasping the lens with the forceps, wherein the lens is held in a folded position within the loop of the apparatus;
   (g) inserting the lens into the eye with the forceps through an incision in the eye, wherein the tail of the apparatus extends outside the eye; and
   (h) pulling the tail of the apparatus to release the lens from the loop of the apparatus.

10. The method of claim 9, wherein step (c) further comprises the steps of grasping the lens from below and pulling the lens into said groove using a forceps positioned through said protrusion and step (d) further comprises the step of pulling the folded lens into said protrusion with the forceps.

11. The method of claim 9, wherein step (h) comprises the step of pulling the tail of the apparatus to release the lens from the loop of the apparatus while holding the lens with the forceps, thereby allowing the lens to unfold, wherein the loop slides over the end of the forceps.

12. A method for folding a foldable intraocular lens and inserting the folded lens into a loop using a disk having a groove on a surface of the disk, wherein the groove extends to an edge of the disk, comprising the steps of:
   (a) placing the lens on the disk;
   (b) placing the loop next to the end of the groove at the edge of the disk;
   (c) folding the lens by forcing the lens into the groove; and
   (d) sliding the folded lens along the groove into the loop.

13. The method of claim 12, wherein the disk further comprises a hollow protrusion at the end of the groove at the edge of the disk, step (b) comprises the step of placing the loop over the protrusion, and step (d) comprises the steps of:
   (1) sliding the folded lens along the groove into the protrusion; and
   (2) slipping the loop off the protrusion and onto the folded lens.

14. The method of claim 13, wherein step (c) further comprises the steps of grasping the lens from below and pulling the lens into the groove using a forceps positioned through the protrusion and step (d)(1) further comprises the step of pulling the folded lens into the protrusion with the forceps.

15. A method for inserting a foldable intraocular lens into an eye using a forceps and an apparatus having a loop and a tail, comprising the steps of:
   (a) grasping the lens with the forceps, wherein the lens is held in a folded position within the loop of the apparatus;
   (b) inserting the lens into the eye with the forceps through an incision in the eye; and
   (c) sliding the loop off the lens while remaining intact as a loop by pulling the tail of the apparatus to release the lens from the loop of the apparatus.

16. The method of claim 15, wherein the tail of the apparatus extends outside the eye through said incision.

17. The method of claim 16, wherein step (c) comprises the step of pulling the tail of the apparatus to release the lens from the loop of the apparatus while holding the lens with the forceps, thereby allowing the lens to unfold, wherein the loop slides over the end of the forceps.

18. The method of claim 15, wherein step (c) comprises the step of sliding the loop off the lens while remaining intact as a loop by pulling the tail of the apparatus through the incision through which the forceps holds the lens, to release the lens from the loop of the apparatus.

19. A method for inserting a foldable intraocular lens into an eye using a forceps and an apparatus having a loop and a tail, comprising the steps of:

(a) grasping the lens with the forceps, wherein the lens is held in a folded position within the loop of the apparatus;

(b) inserting the lens into the eye with the forceps through an incision in the eye, wherein the tail of the apparatus extends outside the eye through said incision; and (c) pulling the tail of the apparatus to release the lens from the loop of the apparatus while holding the lens with the forceps, thereby allowing the lens to unfold, wherein the loop slides off the lens and over the end of the forceps.

* * * * *

UNITED STATES PATENT AND TRADEMARK OFFICE
CERTIFICATE OF CORRECTION

PATENT NO. : 5,456,687
DATED : October 10, 1995
INVENTOR(S) : Joseph DeVenuto

It is certified that error appears in the above-indentified patent and that said Letters Patent is hereby corrected as shown below:

Title Page, Title, line 2, delete "AND INTRACULAR" and insert therefor --AN INTRAOCULAR--.

Column 3, line 25, after "state" insert --while the lens is grasped with a forceps and inserted into the eye through an incision in the eye--.

Signed and Sealed this

Twenty-ninth Day of April, 1997

Attest:

BRUCE LEHMAN

Attesting Officer

Commissioner of Patents and Trademarks